United States Patent
Samain et al.

(10) Patent No.: US 6,953,584 B1
(45) Date of Patent: Oct. 11, 2005

(54) COSMETIC COMPOSITIONS BASED ON ORGANIC SILICON COMPOUNDS COMPRISING AT LEAST A NON BASIC SOLUBILISING FUNCTION

(75) Inventors: Henri Samain, Biévres (FR); Isabelle Rollat, Boulogne-Billancourt (FR); Valérie Jeanne Rose, Paris (FR); Clément Sanchez, Gif-sur-Yvette (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/089,193

(22) PCT Filed: Sep. 27, 1999

(86) PCT No.: PCT/FR99/02290

§ 371 (c)(1),
(2), (4) Date: Jun. 27, 2002

(87) PCT Pub. No.: WO01/22931

PCT Pub. Date: Apr. 5, 2001

(51) Int. Cl.$^7$ ............... A61K 7/00; A61K 7/06; A61K 31/74
(52) U.S. Cl. ............ 424/401; 424/70.1; 424/78.02; 424/78.08; 424/400
(58) Field of Search .............. 424/70.1, 78.02, 424/78.08, 400, 401

(56) References Cited

U.S. PATENT DOCUMENTS

| | | | |
|---|---|---|---|
| 3,914,416 A | 10/1975 | Gueyne et al. | 424/184 |
| 5,750,092 A | 5/1998 | Meyer et al. | 424/59 |
| 6,172,250 B1 | 1/2001 | Seguin et al. | 556/407 |

FOREIGN PATENT DOCUMENTS

| | | |
|---|---|---|
| CH | 535 579 | 4/1973 |
| EP | 0 242 855 | 10/1987 |
| EP | 0 279 623 | 8/1988 |
| EP | 0 464 835 | 1/1992 |
| EP | 0 655 453 | 5/1995 |
| EP | 0 877 027 | 11/1998 |
| FR | 2 746 008 | 9/1997 |
| JP | 63-307811 | 12/1988 |
| WO | 79/00454 | 7/1979 |
| WO | 89/04163 | 5/1989 |

*Primary Examiner*—Shelley A. Dodson
(74) *Attorney, Agent, or Firm*—Steptoe & Johnson LLP

(57) ABSTRACT

The invention comprises, in a cosmetically acceptable aqueous medium, at least 0.02 weight percent relative to the composition total weight, one or several water soluble organosilicon compounds, having one, two or three silicon atoms, at least a non-basic solubilizing function and at least two hydroxyl groups or groups capable of being hydrolyzed per molecule. The invention is applicable to hair care compositions.

9 Claims, No Drawings

COSMETIC COMPOSITIONS BASED ON ORGANIC SILICON COMPOUNDS COMPRISING AT LEAST A NON BASIC SOLUBILISING FUNCTION

The present invention relates generally to aqueous cosmetic compositions, in particular for treating the hair, comprising unpolymerized or relatively unpolymerized, water-soluble organosilicon compounds.

It is common practice to use organic compounds such as polymers to prepare cosmetic compositions for treating the hair. For example, polymers are used that give, on drying, solid materials for fixing the hairstyle in a shape. Such materials are also used to give shape-holding effects. Polymer compounds are also used, such as polysiloxanes, to give haircare effects, particularly to damaged hair or hair that is difficult to disentangle. Cosmetic compositions containing these polymers are applied to the hair and left to dry or rinsed out before proceeding to dry.

The use of polymer compounds presents many drawbacks.

The first drawback lies in the fact that, when the polymers are used in compositions above a certain concentration, the compositions obtained are difficult to apply due to the increase in the viscosity of the compositions. This difficulty in applying the compositions leads to the hair being overloaded in certain areas and thus to cosmetic defects and also involves certain parts of the hair receiving less of the compositions, which, in the end, induces a reduced effect on these areas.

The second drawback lies in the fact that these compositions are occasionally difficult to use. Specifically, polymer compounds of low water solubility require the use of an organic solvent or a mixture of organic solvents. The use of an organic solvent entails several problems, for instance environmental problems and problems affecting the cosmetic quality of the hair.

To overcome these drawbacks, attention has thus turned toward the use of polymer compounds that have been made partially water-soluble. Thus, certain polymer compounds may be used in water without adding any co-solvent. In this case, the limitation lies in the fact that these polymer compounds are partially, or even totally, removed by rinsing the hair. Consequently, in this case, the effect due to the polymer compounds is very limited after rinsing. Ultimately, this limits the effect of rinse-out treatments (shampooing, conditioning), but also reduces the advantage of such compositions used in leave-in mode (hairsetting lotions, mousses, lacquers, etc.) since the user loses the effect acquired by the treatment when the user washes the hair.

Efforts have thus been devoted toward finding compounds for formulating cosmetic compositions that can be used in water and that retain their effect when the hair is rinsed.

Thus, U.S. Pat. No. 4,344,763 (Gillette) describes cosmetic compositions comprising an organosiloxane monomer such as an aminoalkylalkoxysilane and an organic titanate dissolved in an alcohol.

More specifically, the patent describes a process for shaping the hair which consists in moistening the hair with water and then in applying a solution containing, in isopropanol, from 0.5% to 15% by weight of an aminoalkylalkoxysilane and from 0.005% to 1.5% by weight of an organic titanate, and then in placing the hair in the desired shape.

According to this process, it is particularly recommended to keep the isopropanol solution protected from any moisture.

A process has also been disclosed, in EP 113 992, for simultaneously fixing and conditioning the hair using a composition that is stable in the absence of moisture, containing (A) a siloxane oligomer containing at least one nitrogen-hydrogen bond, and (B) an anhydrous, readily hydrolyzable additive chosen from titanates, zirconates, vanadates, germanates, and mixtures thereof.

The solvent for the composition is an aliphatic hydrocarbon or an aliphatic halohydrocarbon, preferably 1,1,1-trichloroethane.

After applying the composition to the hair, the hair is placed in a humid atmosphere so as to bring about the crosslinking of the siloxane oligomer and of the readily hydrolyzable anhydrous additive.

There is thus a need for a stable cosmetic composition, in particular for treating the hair, which is essentially aqueous and which makes it possible to obtain a sufficient cosmetic effect, in particular for the hair, in rinse-out or leave-in mode.

One subject of the present invention is thus stable, aqueous cosmetic compositions, in particular cosmetic compositions for hair treatment and haircare, which overcome the drawbacks of the prior art.

More specifically, one subject of the present invention is stable, aqueous cosmetic compositions for hair treatment arid haircare, which give the hair a long-lasting styling effect and a pleasant feel.

The inventors have found, surprisingly, that it is possible to formulate cosmetic compositions not requiring the use of an organic solvent and having an effective, rinse-fast cosmetic effect, without the risk of problems of the hair being charged in the event of overloading, by using in these compositions unpolymerized or relatively unpolymerized, water-soluble organosilicon compounds comprising at least one nonbasic solubilizing chemical function.

It has been observed that when such compositions are applied, pronounced cosmetic effects are obtained without any problems in the event of overloading, and the effects of which are very rinse-fast and wash-fast.

According to the invention, the cosmetic compositions, in particular for treating the hair, comprise, in a cosmetically acceptable aqueous medium, at least 0.02% by weight, relative to the total weight of the composition, of one or more unpolymerized or relatively unpolymerized, water-soluble organosilicon compounds chosen from organosilanes comprising one silicon atom and organosiloxanes comprising two or three silicon atoms, the organosilicon compounds also comprising at least one nonbasic solubilizing chemical function and at least two hydrolyzable or hydroxyl groups per molecule.

The organosilicon compounds according to the invention are capable of forming, in aqueous medium, a nonhybrid compound, after self-condensation and evaporation of the support. The expression "nonhybrid compound" means a compound that is chemically homogeneous as regards silicon, that is to say that it contains no other additional metallic or organometallic species.

The unpolymerized or relatively unpolymerized organosilicon compounds that are useful in compositions of the present invention are chosen from water-soluble organosilanes comprising one silicon atom and water-soluble organosiloxanes comprising two or three silicon atoms, preferably two silicon atoms. They must also comprise at least one nonbasic solubilizing chemical function, and preferably only one such nonbasic solubilizing chemical function. The nonbasic solubilizing chemical function may be any nonbasic function and in particular any nonamino function that facilitates the solubilization of the organosilicon compound in water. Among the nonbasic solubilizing functions that may be mentioned are carboxylic acids and their salts, quaternary ammoniums, sulphonic acids and their salts and poly(alkyl ether) residues such as poly(oxyalkylene) residues, for example, poly(ethylene oxide) and poly(propylene oxide) and polyglycols, polyacrylamides and acrylamides, and polyols (including natural polyols).

The organosilicon compounds that are useful in the compositions of the present invention also comprise at least two hydrolyzable or hydroxyl groups per silicon atom. The hydrolyzable groups are preferably alkoxy, aryloxy or halogen groups. They may also optionally comprise other chemical functions such as acid or amine functions.

When the unpolymerized or relatively unpolymerized silicon compound according to the invention comprises a nonhydrolyzable group, this group may also comprise a chemical function such as an acid or amine function.

The organosilanes that are preferred according to the invention correspond to the formula:

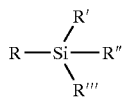

in which:
R' represents a halogen or an $OR_1$ or $R_0$ group;
R" represents a halogen or an $OR_2$ or $R'_0$ group;
R'" represents a halogen or an $OR_3$ or $R''_0$ group;
at least two of the groups R', R" and R'" being other than groups $R_0$, $R'_0$ and $R''_0$;
R is a saturated or unsaturated, linear or branched hydrocarbon-based group comprising a nonbasic, in particular nonamino, solubilizing chemical function;
$R_1$, $R_2$, $R_3$, $R_0$, $R'_0$ and $R''_0$ represent, independently of each other, a saturated or unsaturated, linear or branched hydrocarbon-based group optionally bearing additional nonbasic solubilizing chemical groups, $R_1$, $R_2$ and $R_3$ also possibly denoting hydrogen.

Preferably, $R_1$, $R_2$, $R_3$, $R_0$, $R'_0$ and $R''_0$ represent a $C_1$ to $C_{12}$ alkyl group, a $C_6$ to $C_{14}$ aryl group, a $(C_1$ to $C_8)$alkyl$(C_6$ to $C_{14})$aryl group and a $(C_6$ to $C_{14})$aryl$(C_1$ to $C_8)$alkyl group.

The organosiloxanes that are preferred in the compositions of the present invention may be represented by the formula:

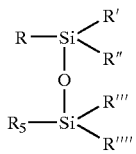

in which:
R" represents a halogen or a group $OR_2$;
R, $R_2$, R' and R'" are defined as above, and R"" represents a halogen, an $OR_4$ group or an $R'''_0$ group;
$R_5$ represents a halogen, an $OR_6$ group or an R"" group;
$R_4$, $R_6$, $R'''_0$ and $R''''_0$ represent a saturated or unsaturated, linear or branched hydrocarbon-based group optionally bearing additional nonbasic solubilizing chemical groups, $R_4$ and $R_6$ also possibly denoting hydrogen; at least one of the groups R'", R"" and $R_5$ being other than $R''_0$, $R'''_0$ and $R''''_0$.

Preferably, $R_4$, $R_6$, $R_0$, $R''_0$, $R'''_0$ and $R''''_0$ represent a $C_1$ to $C_{12}$ alkyl group, a $C_6$ to $C_{14}$ aryl group, a $(C_1$ to $C_8)$alkyl$(C_6$ to $C_{14})$aryl group or a $(C_6$ to $C_{14})$aryl$(C_1$ to $C_8)$alkyl group; and $R_5$ preferably represents a $C_1$ to $C_{12}$ alkyl group, a $C_1$ to $C_{12}$ alkoxy group, a $C_6$ to $C_{14}$ aryl group, a $(C_1$ to $C_8)$alkyl$(C_6$ to $C_{14})$aryl group or a $(C_6$ to $C_{14})$aryl$(C_1$ to $C_8)$alkyl group.

Preferably, the halogen is chlorine.

The groups R are preferably chosen from carboxylic acids and their salts, quaternary ammoniums, sulphonic acids and their salts, and polyalkyl ethers.

Among the carboxylic acid functions and their salts, mention may be made of saturated monoacid radicals such as acetic acid, propionic acid, butyric acid, isobutyric acid, valeric acid and isovaleric acid, saturated diacids such as oxalic acid, malonic acid, succinic acid, glutaric acid and adipic acid, unsaturated monoacids such as acrylic acid, methacrylic acid, crotonic acid, maleic acid, fumaric acid and citraconic acid, carbocyclic acids such as benzoic acid, phthalic acid, isophthalic acid and terephthalic acid, hydroxy and alkoxy carboxylic acids such as glycolic acid, lactic acid, tartaric acid and salicylic acid, and salts of these acids, in particular the alkali metal salts and more particularly the sodium and potassium salts of these acids.

Among the quaternary ammoniums functions that may be mentioned are tetraalkylammoniums and quaternary alkylarylammoniums, the alkyl and/or aryl groups possibly comprising functions such as acid, hydroxyl, amine and halogen functions, and cyclic and heterocyclic quaternary ammoniums.

Among the sulphonic acids and their salts, mention may be made of alkylsulphonic acids such as methylsulphonic acid, arylsulphonic acids such as phenylsulphonic acid, alkoxysulphonic acids such as ethoxysulphonic acid, alkylaryl- and arylalkylsulphonic acids, and salts of these acids, in particular the alkali metal salts of these acids and more particularly the sodium and potassium salts of these acids.

Among the alkyl ether residues that may be mentioned are poly(oxyethylenes), poly(oxypropylenes), poly(oxytetramethylenes) and polyglycols such as poly(ethylene glycol) and poly(propylene glycol).

Another important aspect of the compositions according to the invention is that they contain large amounts of unpolymerized or relatively unpolymerized organosilicon compounds, that is to say compounds comprising one, two or three silicon atoms Thus, it is necessary for the composition to contain, relative to the total weight of the composition, at least 0.02% of unpolymerized or relatively unpolymerized organosilicon compounds and preferably at least 0.5% by weight, possibly ranging up to 50% by weight.

The content of unpolymerized or relatively unpolymerized organosilicon compounds according to the invention is determined by the usual analysis methods such as silicon-29 and proton NMR spectroscopy, and by chromatography.

The compositions according to the invention are aqueous compositions. However, it is possible, for example for the use of adjuvants, to add a cosolvent such as an alcohol or a ketone, for example ethanol or acetone.

In a known manner, all the compositions of the invention may contain adjuvants commonly used in cosmetics, such as oils, waxes or other common fatty substances; standard gelling agents and/or thickeners; emulsifiers; moisturizers; emollients; sunscreens; hydrophilic or lipophilic active agents, for instance ceramides; free-radical scavengers; surfactants; polymers; proteins; bactericides; sequestering agents; antidandruff agents; antioxidants; preserving agents; fragrances; fillers; dyestuffs.

The amounts of these various adjuvants are those conventionally used in the field under consideration.

Needless to say, a person skilled in the art will take care to select the optional compound(s) added to the composition according to the invention such that the advantageous properties intrinsically associated with the composition in accordance with the invention are not, or are not substantially, adversely affected by the envisaged addition.

The compositions according to the invention may be used in rinse-out or leave-in mode.

The compositions according to the invention may be in any form that is suitable for topical application, especially in the form of solutions of the lotion or serum type; in the form of aqueous gels; in the form of emulsions obtained by dispersing a fatty phase in an aqueous phase (O/W) or, conversely, (W/O), of more or less thick liquid consistency such as more or less unctuous milks and creams.

These compositions are prepared according to the usual methods.

The compositions according to the invention are preferably used as hair products, especially for holding the hairstyle or for shaping the hair. They may also give the hair a temporary coloration or provide the hair with good protection against the effects of UV radiation, while at the same time providing hair holding or fixing properties.

The hair compositions according to the invention are preferably styling products such as hairsetting gels or lotions, blow-drying lotions, and fixing and styling compositions such as lacquers or sprays.

The lotions may be packaged in various forms, especially in vaporizers, in pump-dispenser bottles or in aerosol containers to allow an application of the composition in vaporized form or in the form of a mousse. Such packaging forms are indicated, for example, when it is desired to obtain a spray or mousse for fixing or treating the hair.

A subject of the present invention is also the use of the composition according to the invention in a process for treating the hair, in order to hold and/or color it.

According to one embodiment of this process, the composition is applied to rinsed or unrinsed hair, preferably in the form of a spray, either using a pump-dispenser bottle or using an aerosol.

After spraying onto the head of hair, the composition is left to act and to dry.

The hair may be placed in the desired shape, either before the application or immediately after.

The drying time may be variable and depends on the nature of the composition.

After combing, the hair has a very pleasant feel quality.

The invention is illustrated by the examples that follow.

EXAMPLE 1

The formulation below was prepared:

| Composition | Water-soluble unpolymerized or relatively unpolymerized silicon compound | Water |
| --- | --- | --- |
| 1 | Sodium N-[(3-trimethoxysilyl)propyl]ethylenediaminetriacetate neutralized with HCl (pH 6.9) (supplied by the company Gelest) (g per 100 g of composition) 10 g (Active material) | qs 100 g |

Composition 1 is introduced into a container that is fitted with a spraying system of the pump-dispenser bottle type.

Two wigs of 15 g of natural hair are prepared. The hairs are held at the roots on a rubber band and left free over the remainder of the length.

The composition is sprayed onto the first wig (2 g). This wig is then left until dry. The other wig, serving as the comparison, is also left at rest.

The cosmetic properties and in particular the styling effect are noted.

The hairs are then washed with a sodium lauryl ether sulphate shampoo, and then dried again.

The cosmetic properties are noted a second time.

| Wig | Styling effect before washing | Styling effect after washing |
| --- | --- | --- |
| 1 | 30 | 15 |
| 2 (comparative) | 0 | 0 |

The results show that the application of a composition according to the invention to the hair gives it a styling effect that is wash-fast.

What is claimed is:

1. A cosmetic composition comprising, in a cosmetically acceptable aqueous medium, at least 0.02% by weight, relative to the total weight of the composition, of at least one substantially unpolymerized, water-soluble organosilicon compound, the organosilicon compound being a silane having one silicon atom or a siloxane having two or three silicon atoms, the organosilicon compound also having at least one nonbasic solubilizing chemical function and at least two hydroxyl or hydrolyzable groups per molecule.

2. The cosmetic composition of claim 1, wherein the organosilicon compound represents at least 0.5% by weight of the composition.

3. The composition of claim 1, wherein the nonbasic solubilizing chemical function is a carboxylic acid or its salt, a quaternary ammonium, a sulphonic acid or its salt, a poly(alkyl ether), a polyacrylamide or acrylamide, or a polyol.

4. The composition of claim 1, wherein the hydrolyzable groups are alkoxy, aryloxy or halogen groups.

5. The cosmetic composition of claim 1, wherein the organosilicon compound has the formula:

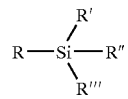

in which;
R' represents a halogen or an $OR_1$ or $R_0$ group;
R" represents a halogen or an $OR_2$ or $R'_0$ group;
R'" represents a halogen or an $OR_3$ or $R''_0$ group;
at least two of the groups R', R" and R'" being other than the groups $R_0$, $R'_0$ and $R''_0$;
R is a saturated or unsaturated, linear or branched hydrocarbon-based group comprising a nonbasic solubilizing chemical function;
$R_0$, $R'_0$, $R''_0$, $R_1$, $R_2$ and $R_3$ represent, independently of each other, a substituted or unsubstituted, saturated or unsaturated, linear or branched hydrocarbon-based group, the optional substituent being an additional nonbasic solubilizing chemical group; and
$R_1$, $R_2$ and $R_3$ may represent, independently of each other, hydrogen.

6. The cosmetic composition of claim 1, wherein the organosilicon has the formula:

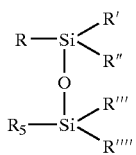

in which:

R'' represents a halogen or an $OR_2$ group;

R' represents a halogen or an $OR_1$ or $R_0$ group;

R''' represents a halogen or an $OR_3$ or $R''_0$ group;

R is a saturated or unsaturated, linear or branched hydrocarbon-based group comprising a nonbasic solubilizing chemical function;

$R_0$, $R''_0$, $R_1$, $R_2$ and $R_3$ represent, independently of each other, a substituted or unsubstituted, saturated or unsaturated, linear or branched hydrocarbon-based group, the optional substituent being an additional nonbasic solubilizing chemical group;

$R_1$, $R_2$ and $R_3$ may represent, independently of each other, hydrogen; and R'''' represents a halogen, an $OR_4$ group or an $R'''_0$ group;

$R_5$ represents a halogen, an $OR_6$ group or an $R''''_0$ group;

at least one of the groups R''', R'''' and $R_5$ being other than the groups $R''_0$, $R'''_0$ and $R''''_0$; and $R_4$, $R_6$, $R'''_0$ and $R''''_0$ represent a substituted or unsubstituted, saturated or unsaturated, linear or branched hydrocarbon-based group, the optional substituent being an additional nonbasic solubilizing chemical group; and $R_4$ and $R_6$ may represent, independently of each other, hydrogen.

7. The cosmetic composition of claim 6, wherein $R_1$, $R_2$, $R_3$, $R_4$, $R_6$, $R_0$, $R'_0$, $R''_0$, $R'''_0$ and $R''''_0$ represent a $C_1$ to $C_{12}$ alkyl group, a $C_6$ to $C_{14}$ aryl group, a ($C_1$ to $C_8$)alkyl($C_6$ to $C_{14}$)aryl group or a ($C_6$ to $C_{14}$)aryl($C_1$ to $C_8$)alkyl group.

8. The composition of claim 1, wherein the composition is in the form of a hair product.

9. The composition of claim 8, wherein the composition is in the form of a hair product for holding the hair or for shaping the hair.

* * * * *